(12) United States Patent
Korbonits et al.

(10) Patent No.: US 6,348,470 B1
(45) Date of Patent: Feb. 19, 2002

(54) ANTITUSSIVE COMPOSITIONS

(76) Inventors: Dezsö Korbonits, Vèrhalom u. 27./D., H-1025 Budapest; Péter Arányi, Bimbò ùt 216, H-1026 Budapest; István Jelinek, Jerney u. 28., H-1141 Budapest; Endre Mikus, Ida. u. 96, H-1162 Budapest, all of (HU)

( * ) Notice: Subject to any disclaimer, the term of this patent is extended or adjusted under 35 U.S.C. 154(b) by 0 days.

(21) Appl. No.: 09/381,841

(22) PCT Filed: Mar. 20, 1998

(86) PCT No.: PCT/HU98/00027

§ 371 Date: Sep. 24, 1999

§ 102(e) Date: Sep. 24, 1999

(87) PCT Pub. No.: WO98/42322

PCT Pub. Date: Oct. 1, 1998

(30) Foreign Application Priority Data

Mar. 26, 1997 (HU) .............................................. 9700654

(51) Int. Cl.⁷ .............................................. A61K 31/52
(52) U.S. Cl. ..................... 514/263; 424/464; 424/465; 424/450; 544/274; 544/275
(58) Field of Search ................................ 424/464, 465, 424/450; 544/274, 275; 514/263

(56) References Cited

U.S. PATENT DOCUMENTS

| | | | |
|---|---|---|---|
| 4,187,308 A | * | 2/1980 | Franzone et al. ............ 424/253 |
| 4,840,949 A | | 6/1989 | Korbonits et al. |
| 4,859,658 A | | 8/1989 | Di Schiena et al. |
| 5,009,819 A | * | 4/1991 | Popescu et al. .............. 264/4.1 |
| 5,422,352 A | | 6/1995 | Astrup |
| 5,560,913 A | | 10/1996 | Kupper |
| 5,641,512 A | | 6/1997 | Cimiluca |

FOREIGN PATENT DOCUMENTS

| | | |
|---|---|---|
| FR | 2531339 | 2/1984 |
| WO | 9100730 | 1/1991 |
| WO | 9507103 | 3/1995 |
| WO | 9704808 | 2/1997 |

OTHER PUBLICATIONS

Remington: the science and practice of pharmacy, vol. II, p. 1050, 1995.*

M. Blumenthal, Allergy Proc., vol. 13, No. 6, Nov. 1992–Dec. 1992, pp. 345–352.

J.P. Bonte, Bull. Soc. Pharm., vol. 32, No. 4, 1976, pp. 219–231.

S. Budavari et al, Eds., The Merck Index, twelfth edition, 1996, Merck & Co., Inc., see p. 1583.

G. Zedler, Dialog (R) File 73, Embase, Accession No. 697098, Stomat. DDR, vol. 26, No. 4, 1976, pp. 248–251.

* cited by examiner

*Primary Examiner*—Diana Dudash
*Assistant Examiner*—S Sharareh
(74) *Attorney, Agent, or Firm*—Birch, Stewart, Kolasch & Birch, LLP

(57) ABSTRACT

The invention relates to the use of theobromine and/or its salts and/or its complexes optionally in admixture with other known active ingredients and inert solid or liquid carriers, additives and auxiliary agents for the manufacture of a pharmaceutical composition suitable for relieving cough syndrome. Further subject of the invention is a method of treatment of a human or animal subject being in condition where relieving of cough is desirable which comprise steps of administering in an effective amount theobromine and/or salts and/or its complexes optionally in admixture with other known active ingredients and suitable inert, solid or liquid carriers, additives and auxiliary agents.

5 Claims, 2 Drawing Sheets

ANTITUSSIVE COMPOSITIONS

This application is the national phase under 35 U.S.C. § 371 of PCT International Application No. PCT/HU98/00027 which has an International filing date of Mar. 20, 1998, which designated the United States of America.

The invention relates to antitussive formulations containing theobromine [3,7-dihydro-3,7-dimethyl-1H-purine-2,6-dione] of the formula (III) or its salts or its complexes as antitussive agent.

It is known that the three natural methylxantine alkaloids, namely theophylline of the formula (I), caffeine of the formula (II) and theobromine of the formula (III) are found in the leaves of tea (Thea sinensis), cacao-seed (Theobroma cacao) and coffee-berry (Coffea arabica). These plants have high relevance in human alimentation because they are the source of several widely-consumed goods and beverages.

In tea besides theophylline and theobromine the caffeine is the main alkaloid. In coffee the caffeine is the dominant alkaloid while in cocoa powder and in chocolate-liquor which is the basic material for chocolate, theobromine is the main alkaloid but it also contains some caffeine.

The three natural methylxanthines (I, II, III) have complex biological effects but despite of the close chemical similarity there are significant differences with respect to the strength of efficacy and in the spectrum of their effects.

It is generally accepted in the literature that the wide-spectrum of the pharmacological effects of methylxanthines can be deduced from two main molecular mechanisms. One is the non-specific inhibition of the cyclic nucleotide phosphodiesterases (PDEs) and the second is the antagonism of adenosine receptors. Numerous alkylxanthines have been examined and it is established, as a general rule, that both mentioned effects decrease if there is no substituent on the N1 atom of the xanthine moiety or if the N7 atom contains a substituent, as compared with the corresponding 1,3-dialkylxanthine.

In the case of theobromine the N1 atom is not but the N7 atom is substituted so according to the general rule the activity of the theobromine should be weaker than either that of caffeine or theophylline. Really, the activity rank order of the three naturally occurring methylxanthines in respect of the PDE inhibition and the adenosine antagonism is the following: theophylline>caffeine>theobromine.

It is a very important and a clinically highly relevant feature of the methylxanthines, especially of theophylline, that they relax the different types of smooth muscles both in vivo and in vitro. The bronchial smooth muscle relaxant effect and other excellent therapeutic properties of theophylline are widely used for the treatment of asthma. The similar effects of theobromine and caffeine are much less pronounced than those of theophylline.

It is known and supported by the high popularity of the consumption of tea and caffeine containing beverages that both caffeine and theophylline have strong central nervous system (CNS) stimulating effects. The effect of theobromine on the CNS is weaker than either that of caffeine or theophylline (Mumford, G. K. et al., Psychopharmacology, 1994, 115:1).

Both caffeine and theophylline have strong and complex effects on cardiac muscle and the cardiovascular system, It is known that these compounds have remarkable peripheral vascular dilating effects, but at higher doses they also cause tachycardia. Theobromine has much weaker cardiovascular effects.

The diuretic effect is a very characteristic feature of these methylxantines (I, II, III), especially of theophylline. Theobromine has only a weak diuretic effect compared either to theophylline or caffeine.

The differences, which exist in the useful therapeutic effects of the natural methylxanthines, can be found in their side and toxic effects, too. Due to the narrow therapeutic dose-range of theophylline the risk of the overdosing is high, while it is weaker in the case of caffeine. The risk of dangerous side effects caused by theobromine is negligible compared to either theophylline or caffeine (Stavric, B., Fd.Chem.Toxic. 1988, 26:725).

The scientific literature dealing with naturally occurring methylxanthines especially with theophylline and caffeine is extraordinarily broad. Data can be found in some thousands of scientific papers, patent specifications, reviews and books concerning this topic. These studies suggest that due to the poor biological activity of theobromine, the compound has no therapeutic relevance. The above opinion is supported by one of the most well known pharmacological book:

"Theophylline, caffeine, and theobromine share in common several pharmacological actions of therapeutic interest. They relax smooth muscle, notably bronchial muscle, stimulate the central nervous system (CNS), stimulate cardiac muscle, and act on the kidney to produce diuresis. Since theobromine displays a low potency in these pharmacological actions, it has all but disappeared from the therapeutic scene. "(Rall, T. V., In: Goodman and Gilman's, The Pharmacological Basis of Therapeutics, 8th Ed., p. 620, Pergamon Press, New York, 1990). No reference has been found to the antitussive effect of theobromine.

Figure 1:
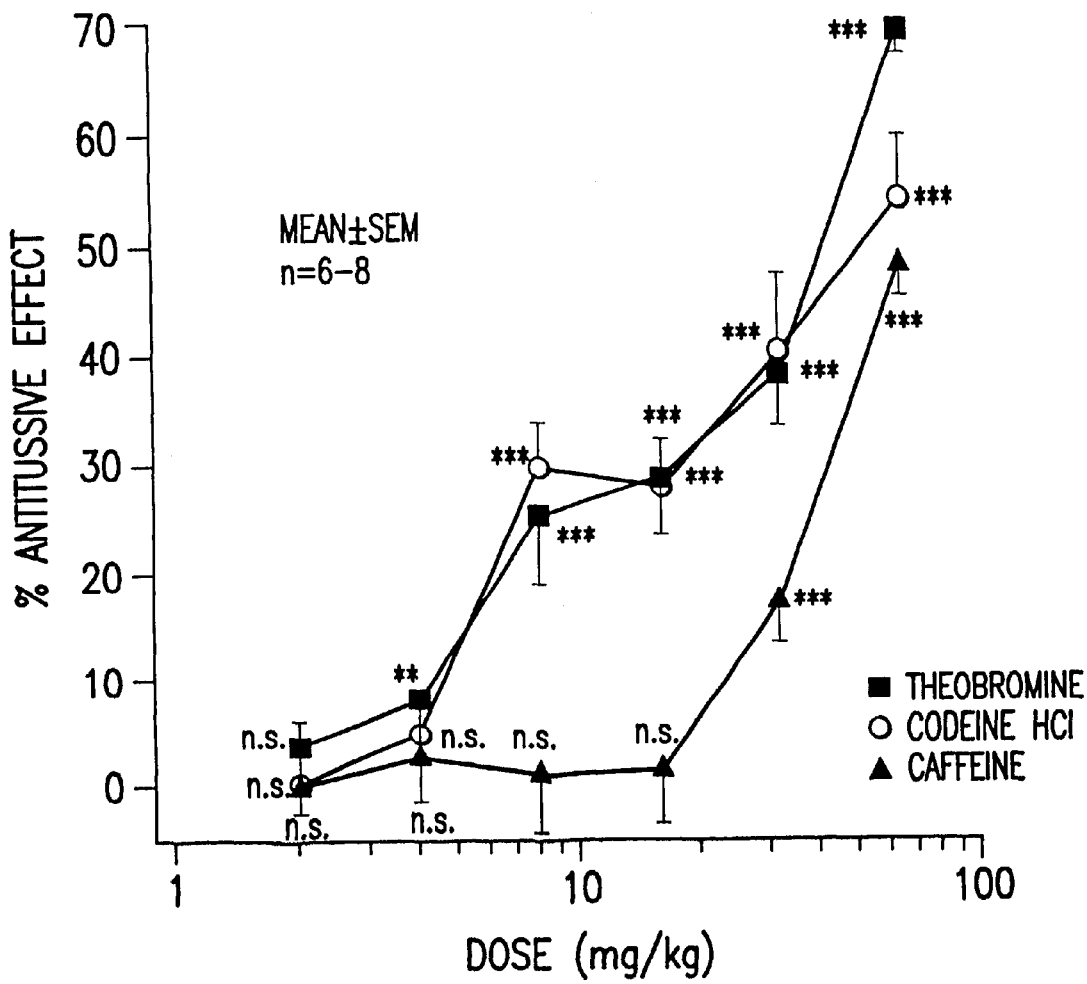
FIG. 1 shows the antitussive effect of theobromine, caffeine and the reference codeine HCI on 15% citric acid spray induced cough model in guinea pig (the results were adjusted to control values). For statistical analysis, Mann-Whitney U test was used; treated groups were compared to the control ones, n.s.=not significant; $p<0.01$; * * * $p<0.001$. The animals were treated orally, one hour before the second cough insult.

With full knowledge of the above facts it was very surprising when we come to the unexpected result that theobromine(III) shows a strong and long lasting antitussive effect. This effect of theobromine is comparable to that of codeine which is one of the most widely used antitussive morphine derivative.

This unexpected and advantageous antitussive effect of theobromine can be used excellently in the therapy, because theobromine has low toxicity and has no dangerous side effects. We emphasise the importance of the fact that as opposed to the morphine structured antitussive compounds, theobromine is free from any breathing depressive effect moreover theobromine has some favourable bronchopulmonary effects in addition to its antitussive effect: according to our present data theobromine significantly stimulates the mucociliary clearance functions similarly to bromhexine, a well known secretolytic drug.

According to the literature theophylline has a weak antitussive activity on citric acid spray-induced cough in guinea pig. This weak antitussive activity can not be improved by increasing the dose of theophylline because of the appearance of harmful side effects (Forsberg, K. et al., Respiration, 1992, 59:72). Aminophylline (theophylline ethylenediamine) is practically ineffective in the same test model at all the tested doses (Franzone, J. S. et al., II Farmaco, Ed.Sc. 1981, 36:201).

Similar antitussive effect has not been demonstrated by caffeine or theobromine. We examined their antitussive activity on the citric acid spray-induced cough model, using codeine-HCl as reference compound.

The experiments for acute antitussive activity were carried out in Hartley albino guinea pigs (Charles River) of either sex, weighing 250–300 g. The method of Tardos was adapted with minor modifications (Tardos, L., Erdély, I., Arzneim. Forsch. (Drug Res.) 1966, 16:617). The spray was generated by a sprayer connected to a transparent chamber (6.7 liter volume). Compressed air with a flow of 0.16 liter/sec and pressure of 0.5 bar produced the spray. The vapour penetrated into the chamber through a short tube driven by constant air flow. The animals were put into the transparent chamber individually and exposed to the citric acid (15 w/v % citric acid dissolved in distilled water ) aerosol for 3 minutes. The number of coughs was counted by a trained observer from the start of spray exposure until the end of it. The coughing of the animals was defined as a strong contraction of abdomen which was followed by forced expiration through the opened mouth of the animals. For testing a substance, only animals which showed equal or more than 6 coughs during 3 minutes during the first trial were used. The selected animals were treated once orally with the studied xanthines or the reference codeine as a suspension in 0.1% methylcellulose (treated groups) or with 0.1% methylcellulose alone (control group). The vehicle in a volume of 0.1 ml/100 g body weight was applied. The second citric acid insult was evoked 1 hour after test substance treatment. The antitussive activity was calculated as the percentage decrease of the number of coughs between the second and the first challenge. The drug treated groups were compared to the vehicle treated control groups.

As indicated in FIG. 1. theobromine and the reference codeine dose-dependently decreased the cough number after single oral treatment.

The antitussive effect of theobromine was as strong as the effect of codeine. The antitussive effect of theobromine and codeine was already significant at 4 and 8 mg/kg dose, respectively. A strong decrease (69.0±1.9%) of cough number was reached with 64 mg/kg dose of theobromine. The same dose of codeine decreased the cough number a slightly lesser degree (54.2±5.7%). The calculated $ED_{50}$ values of theobromine and codeine were 37 mg/kg and 49 mg/kg , respectively. On the contrary, caffeine has no antitussive effect in the dose-range of 2–16 mg/kg. In higher doses (32 and 64 mg/kg) caffeine significantly decreased the cough number (17.5±3.7% and 48.4±3.1%, respectively), but these doses are close to the toxic dose of the compound, so the antitussive effect of caffeine is not relevant in the therapy.

The acute oral toxicity of the three compounds in rats are the following ($LD_{50}$ mg/kg): caffeine: 192; theobromine: 1265; codeine: 427 (The Sigma-Aldrich Library of Chemical Safety Data, ed. Lenga R. E., Edition II., Sigma-Aldrich Corporation, USA, 1988).

From the given $ED_{50}$ and $LD_{50}$ values calculated antitussive therapeutic index ($LD_{50}/ED_{50}$) of theobromine is 34 and that of codeine is 8.7. The antitussive therapeutic index of theobromine is roughly 4 times higher than that of codeine.

Figure 2:
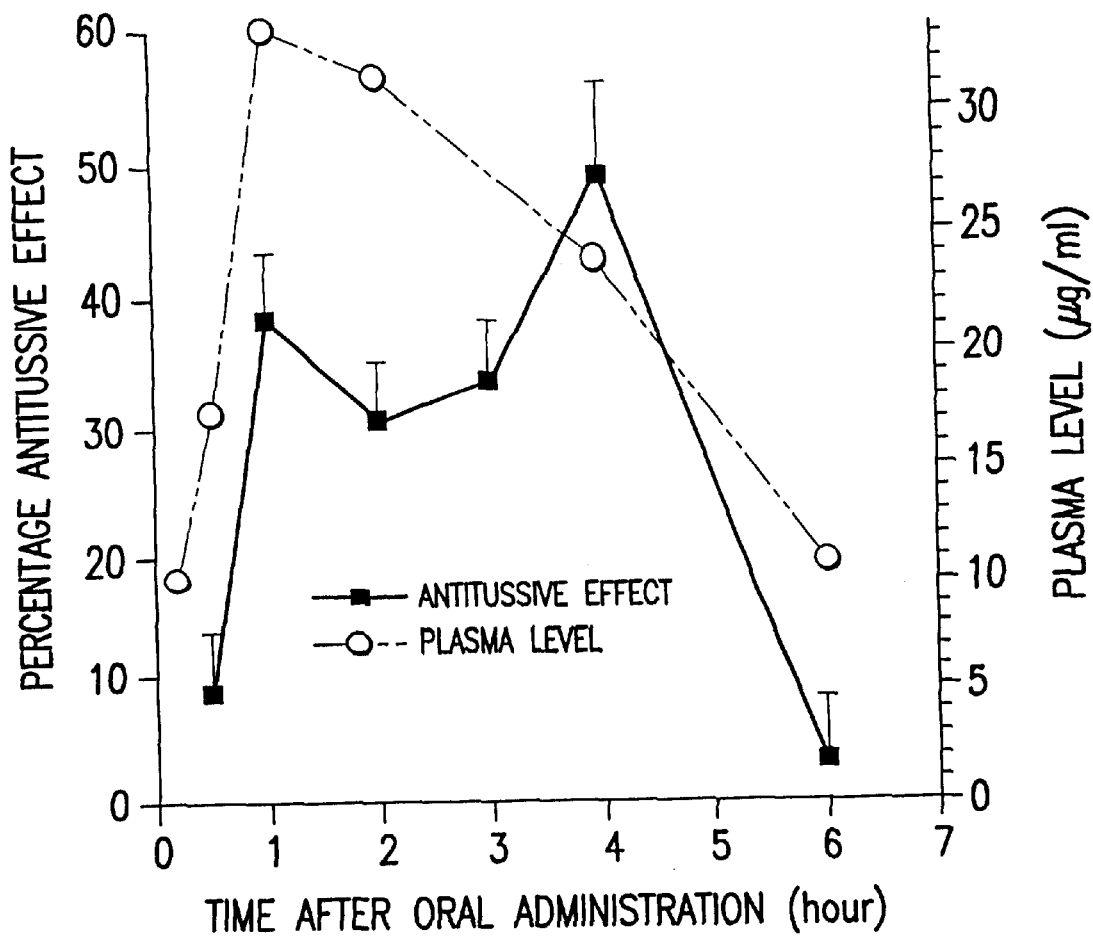

It was justified by further experiments that the excellent antitussive effect of theobromine exists for several hours. The time-dependency of the antitussive effect of 32 mg/kg p.o. administered theobromine on Hartley guinea pigs was determined as specified in the 1 hour acute experiments.
As shown in FIG. 2., theobromine has a long-lasting antitussive activity.

The time course of the p.o. 32 mg/kg theobromine induced antitussive effect is roughly parallel with the time-course of the plasma-level of theobromine measured also in 32 mg/kg oral dose in guinea pigs (See FIG. 2.). Demonstrating this close parallelism between these two time-courses is very important and advantageous regarding to the topic of our invention. Reaching the expected therapeutic effect within a short time after oral administration of a drug is an important feature. The results of a recent human trial showed that chocolate-based theobromine formulation significantly improved both the rate of the intestinal absorption and the plasma concentration of theobromine compared to a pure theobromine containing capsule, using equivalent theobromine doses in both formulations. The maximal plasma level of theobromine was reached three hours after the administration of the capsule, while using a chocolate-based formulation the absorption was much quicker reaching the maximal plasma concentration two hours after the treatment (Mumford, G. K. et al., Eur.J.Clin.Pharmacol. 1996, 51:319). We have to emphasise that the decrease in the theobromine plasma level 4 hours after the treatment in guinea pig is relatively steep while in human theobromine plasma half-life is prolonged ($t_{1/2}$=6.1–10 hours; Shively, C. A. et al., Clin.Pharmacol.Ther. 1985, 37:415). The half-life of codeine in human plasma is much shorter: 2–4 hours (Raisine T., Pasternak G., In: Goodman and Gilman's The pharmacological Basis of Therapeutics, 9th Ed., Mc Graw-Hill, New York, 1996, p. 534).

It is as well worth mentioning that the human plasma level decrease of theobromine is slower than that of theophylline or caffeine (Birkett, D. J., Methylxanthine metabolism in man. In: Anti-asthma xanthines and adenosine, p. 235. Eds. Andersson K. E. and Persson C. G. A., Excerpta Medica, Amsterdam, 1985).

The close connection between theobromine plasma level and its antitussive effect in guinea pig unambiguously suggests a long-lasting antitussive effect in humans, as well.

Taking into account the dose-response curve of theobromine in guinea pig its advantageous toxicological profile and minimal side effects, the proposed adult antitussive dose of theobromine varies between 200 and 500 mg, two or three times a day.

As mentioned earlier, the chocolate-based formulation of theobromine helps to reach higher plasma level in humans compared to the capsule formulation (Mumford, G. K. et al., Eur.J.Clin.Pharmacol. 1996, 51:319) so we examined whether the required antitussive effect could be reached by simply eating common chocolate or not.

It is known that the different types of common chocolates from milk chocolate to dark-chocolate contain different amounts of theobromine. The dark chocolate contains approximately three times more theobromine than the milk one. A special dark chocolate bar (41 g) (Hershey's Special Dark, New and Improved) contains 185 mg theobromine and 36 mg coffeine (Mumford, G. K. et al., Eur.J.Clin.Pharmacol. 1996, 51:319). This means that for reaching the needed antitussive effect one has to eat at least 1–3 bars of these special dark chocolate (41–123 g), 2–3 times a day. Of course from less theobromine containing chocolates one should consume more bars. Eating so much chocolate especially for a longer period of time (chronic administration) is contraindicated for obvious health reasons. The caffeine content of chocolate, which can cause characteristic CNS stimulating and other pharmacological effects, represents more significant problems (Mumford, G. K., et al., Psychopharmacology, 1994, 115:1).

If we want to apply the antitussive doses of theobromine in common cocoa-products, (cocoa-drinks and cocoa-containing food-products) the situation is similar as in the case of chocolate, on the basis of the theobromine and caffeine content of the different cocoa-products (Zoumas, B. L., Methylxanthine composition and consumption patterns of cocoa and chocolate products, in: CAFFEINE, ed. Spiller, G., CRC Press, USA, 1997).

The molecular mechanism of the strong antitussive effect of theobromine (which is much better than the antitussive effect of both caffeine and theophylline) is not known. As we have noted earlier, this effect is really surprising because all the other effects of theobromine fall behind of those of the other two naturally occurring xanthine derivatives.

We suggest that several complex effects of methylxanthines play a role in the antitussive effect. The extremely good antitussive activity of theobromine is probably caused by the fact that from the complex and multistep effects the adenosine receptor (primarily A1) antagonistic effect is significantly weaker than that of either theophylline or caffeine.

Some experiments have been carried out for habit formation studies. The aim of these experiments was to check whether the antitussive activity of theobromine remained constant after repeated (chronic) administration of the drug. The same method was adapted as described above. Selected Hartley albino guinea pigs were treated once a day for 14 days with 32 mg/kg theobromine as a suspension in 0.1% methylcellulose (treated group) or with 0.1% methylcellulose alone (control group). The antitussive effect was tested on Day1-Day7-Day14. The cough number was counted just before and 1 hour after the treatment on the indicated days. The control group (n=12) underwent the same protocol as the theobromine treated group (n=13).

The antitussive effects adjusted to the control values, on Day1, Day7 and Day4 were 46.1±2.3%, 54.1±3.4% and 49.0±4.9%, respectively. The antitussive activity of theobromine in guinea pigs was not reduced by habit formation even after 14 consecutive days of treatment of high (32 mg/kg) oral doses.

Note, that in men relatively high daily doses of theobromine administered in the form of dark chocolate (6 mg/kg/day) for one week altered neither the metabolism of theobromine nor its clearance (Shively, C. A., et al., Clin.Pharmacol. Ther. 1985, 37:415).

In connection with the metabolism of theobromine it should also be noted that according to our experiments 3-methylxanthine, the main metabolite of theobromine, has some antitussive effect in a narrow dose range. However, at higher doses the dose-activity curve breaks down.

Mucociliary clearance, the major defence mechanism of respiratory airways, is significantly impaired by chronic bronchitis (Dirksen, H., et al., Eur.J.Respir-Dis. 1987, 71(Suppl. 153):145). Patients with bronchitis are among those who most frequently use antitussive drugs. Traditional opioide antitussives, such as codeine, not only impair the respiratory parameters, but exert a depressing action on mucociliary clearance, as well (Melville, G. N., Iravani, J., Can.J.Physiol.Pharmacol. 1975, 53:1122). Note, that in humans and in in vitro animal experiments theophylline has a significant mucociliary clearance-improving activity (Wanner, A., Am.J.Med. 1985, 79(Suppl. 6A):16; Wagner, U., et al., Eur.J.Pharmacol., 1996, 298:265). The aim of our studies was to investigate whether theobromine (which as opposed to theophylline has a strong antitussive activity, similar in strength to that of codeine) influences the mucociliary clearance of respiratory airways in rabbits. To investigate the effect of theobromine of mucociliary clearance activity the method of Achterrath-Tuckerman was adapted (Achterrath-Tuckeiman, U., et al., Lung, 1992, 170:201). Bromhexine-HCl, a known secretolytic agent was used as reference substance.

This model involves the administration of $^{99m}$Technecium-labelled homologues red blood cell suspension by inhalation. Theobromine and the reference agent bromhexine were administered intravenously 30 min before the inhalation of the labelled red blood cells. After the last inhalation of the nebulized cell suspension, the radioactivity was measured with a gamma-camera over the closed chest for a period of 60 min. The time-activity curves were generated and fitted to the measured points. The mucociliary clearance value was given as the amount of radioactive marker in percent elimination in unit of time (hour) The increase in mucociliary clearance value indicated quantitatively if the mucociliary activity has been enhanced by the previous drug treatment. For statistical evaluation the drug treated groups were compared to the vehicle treated group using Student's t test. Intravenous theobromine at doses 2, 4 and 8 mg/kg dose-dependently increased the mucociliary clearance. The highest injected dose of theobromine (8 mg/kg) resulted a 60% ($p<0.05$) increase in clearance. 20 mg/kg bromhexine could evoke similar clearance.

Theobromine significantly increased the mucociliary clearance function in rabbits in the antitussive dose-range established in our earlier mentioned studies.

Antitussives are generally given to disrupt the harmful irritation cough, which lead to the vicious circle of cough-irritation-cough.

It has to be emphasised, that a complete or even a too strong inhibition of cough is undesirable because this suppresses productive cough, too. An ideal antitussive drug would reduce the frequency of cough and render it less distressing but would leave the cough reflex unimpaired, in other words, the ideal antitussive is able to inhibit harmful cough but does not impair useful cough. In addition, the ideal antitussive agent has bronchodilator activity, stimulates the mucociliary clearance functions, and has no toxic side effects.

Theobromine seems to fulfil all the above mentioned requirements. According to our invention theobromine can be used advantageously for the treatment of different diseases as an antitussive drug. Taking into account its secretolytic effect it could be especially useful in the medication of airways diseases (bronchitis, flue etc.) alone or in combinations.

Based on the above the invention relates to pharmaceutical composition suitable for relieving cough syndrome comprising a therapeutically active amount of theobromine of the formula (III) and/or its salts and/or its complexes optionally in admixture with other known active ingredients and inert, solid or liquid carriers, additives and auxiliary agents.

A further aspect of our invention is the use of theobromine and/or its salts and/or its complexes optionally in admixture with other known active ingredients and inert, solid or liquid carriers, additives and auxiliary agents for the manufacture of a pharmaceutical composition suitable for relieving cough syndrome.

Method of treatment of a human or animal subject being in a condition where relieving of cough is desirable which comprises the step of administering in an effective amount theobromine and/or its salts and/or its complexes optionally in admixture with other known active ingredients and suitable inert solid or liquid carriers, additives and auxiliary agents belongs also to the subject of the invention.

For producing theobromine containing drugs or paramedicines different formulations are suitable, for example injection, syrup, dragée, tablet, pastille, suppository, capsule and retard forms of all of these such as liposomes. On the basis of the human absorption data the chocolate based pastille and dragée formulations, especially the theobromine enriched chocolate products and the liposomes are promising. Preferably the theobromine and/or its salt and/or complex is used for the manufacture of a pharmaceutical composition suitable for relieving cough syndrome partly or totally as ingredient of cocoa powder, instant cocoa or chocolate. The listed formulations according to the invention are produced by using conventional pharmaceutical and alimentary technics. The theobromine content of the drug formulations for utilising our invention is 0.1–99.9 w/w %, preferably 1–30 w/w %. The daily dose, depending on the age of the patients and the route of administration, is 10–3000 mg.

The invention is supported with the following formulation examples without restricting the use of theobromine as an antitussive agent to these examples.

| Example 1. Tablet: | |
|---|---|
| Theobromine | 500 g |
| Corn starch | 130 g |
| Calcium phosphate | 209 g |
| Magnesium stearate | 1.0 g |
| | 840 g |

The blended compounds are granulated by methods known per se, 1000 pieces of 840 mg tablets are compressed, each tablet containing 500 mg of active ingredient.

| Example 2. Depot dragées: | |
|---|---|
| Theobromine | 450 g |
| Carboxy-methyl-cellulose | 300 g |
| Stearic acid | 20 g |
| Cellulose acetate phthalate | 30 g |
| | 800 g |

The active ingredient, the carboxy-methyl-cellulose and stearic acid are blended and granulated with a solution of cellulose acetate phthalate in 200 cm$^3$ ethylacetate-ethanol and 800 mg tablets are compressed coated with a 5% aqueous polyvinyl pyrrolidone solution containing sugar by method known per se. All dragées contain 450 mg of active ingredient.

| Example 3. Capsule: | |
|---|---|
| Theobromine | 350 g |
| Poly-vinyl-pyrrolidone | 200 g |
| Talcum | 60 g |
| Magnesium-stearate | 60 g |
| Sodium-starch-glycolate | 100 g |
| | 770 g |

All ingredients are blended and granulated by method known per se. 1000 capsules are filled with this granulate getting 350 mg active ingredient containing capsules.

| Example 4. Suppository: | |
|---|---|
| Theobromine | 50 g |
| Adeps solidus | 150 g |
| | 200 g |

Adeps solidus is melted and the active ingredient is stirred in it. This suspension is poured to 100 pieces cooled suppository moulds getting 500 mg active ingredient containing suppositories.

| Example 5. Syrup: | |
|---|---|
| Theobromine | 25 g |
| Carboxy-methyl-cellulose | 1 g |
| Saccharose | 30 g |
| Aroma | 0.1 g |
| Colorant | 0.01 g |
| Preservant | 0.01 g |
| Distiiled water | ad 100 g |

40 g distilled water and the saccharose are boiled. Having cooled it down, the aroma, the colorant and the suspended theobromine in swollen carboxy-methyl-cellulose (10 cm$^3$ distilled water+1 g carboxy-methyl-cellulose) are mixed and the syrup is completed to 100 g with distilled water. 1 g of this syrup contains 250 mg active ingredient.

| Example 6. Chocolate pastille: | |
|---|---|
| Theobromine | app. 50 g |
| Cocoa powder | 20 g |
| Saccharose | 20 g |
| Milk powder | 5 g |
| Ethyl-vanillin | 0.01 g |
| Cocoa butter | ad 250 g |

The active ingredient is measured, taking into account the theobromine content of the cocoa powder, to get 50 g theobromine per 250 g chocolate composition. 150 g cocoa butter is melted just above the melting point and the cocoa powder, saccharose, milk powder, ethyl-vanillin and the active ingredient is mixed to it. This suspension is completed to 250 g with melted cocoa butter. This mixture is poured into cooled moulds. 100 chocolate pastilles, each containing 500 mg theobromine, are obtained.

| Example 7. Liposome: | |
|---|---|
| Theobromine salicylate | 15 g |
| Phospholipon 90H | 30 g |
| Ethyl alcohol | 22.5 g |
| Purified water, USP | 82.5 g |

Ingredients combined as per formulation procedure. Temperature of lipid phase is raised to transition temperature of the phospholipid and water is added at equal temperature. The mixture is stirred at approximately 50 RPM for 20 min at 45° C., heat is removed and stirring continued until preparation reaches 25° C.

What we claim is:

1. A method of stimulating mucociliary clearance to alleviate irritable cough comprising administering to a subject, in an antitussive effective amount, theobromine as an antitussive agent and/or its salts optionally in admixture with inert, solid or liquid carriers, additives and auxiliary agents wherein said amount of theobromine is 10–3000 mg, and alleviating irritable cough.

2. The method of claim 1, wherein theobromine and/or its salts are used as an antitussive agent in a dose form of injection, syrup, dragée, tablet, pastille, suppository, capsule and retard form of them.

3. The method of claim 2, wherein said theobromine as an antitussive agent and/or its salts are in the form of a liposome.

4. The method of claim 1, wherein said theobromine as an antitussive agent is represented by formula III:

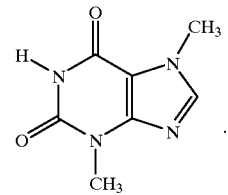

III

5. The method of claim 1, wherein the amount of theobromine as an antitussive agent is 1–30 w/w %.

* * * * *